United States Patent [19]

Koppenhagen et al.

[11] 4,311,643

[45] Jan. 19, 1982

[54] PROCESS FOR PRODUCING METAL CORRINOIDS

[75] Inventors: Volker Koppenhagen, Braunschweig-Stöckheim, Fed. Rep. of Germany; Gerhard Schlingmann, Berkeley, Calif.; Bernd Dresow, Brunswick; Ortrud Ebelmann, Kissenbrück, both of Fed. Rep. of Germany

[73] Assignee: Gesellschaft fur Biotechnologische Forschung mbH, Braunschweig-Stöckheim, Fed. Rep. of Germany

[21] Appl. No.: 127,366

[22] Filed: Mar. 4, 1980

[30] Foreign Application Priority Data

Mar. 6, 1979 [DE] Fed. Rep. of Germany ....... 2908670

[51] Int. Cl.³ ............................................. C09B 47/00
[52] U.S. Cl. ..................................... 260/314; 435/119
[58] Field of Search ......................................... 260/314

[56] References Cited

U.S. PATENT DOCUMENTS 3,846,237 11/1974 Toohey ................................. 435/86

FOREIGN PATENT DOCUMENTS 1642749 3/1971 Fed. Rep. of Germany ........ 435/86

OTHER PUBLICATIONS

Yamada et al, Chem. Abstracts, vol. 65, cols. 7548–7549 (1966), (also p. 942 S).
Shimizu et al, Chem. Abstracts, vol. 65, col. 7549 (1966).
Ladd et al, Chem. Abst., vol. 55, subject index 3305 s and col. 27482 (1961).

*Primary Examiner*—John D. Randolph
*Attorney, Agent, or Firm*—Hammond & Littell, Weissenberger and Muserlian

[57] ABSTRACT

A process for producing red metal corrinoids comprising reacting yellow metal-free corrinoids having main absorptions $\lambda_{max}$ of 480 and 290 nm, in a liquid medium, with complex-forming metal ions to give yellow metal corrinoids, and alkalizing said metal corrinoids by treatment with an alkali.

12 Claims, No Drawings

PROCESS FOR PRODUCING METAL CORRINOIDS

Red metal-free corrinoids can be obtained by microbiological processes which are claimed, for example, in German Offenlegungsschrift No. 1 642 749. Such red corrinoids are used, inter alia, to produce metal corrinoids by introducing into the metal-free corrinoids radio-active cobalt ions or metal ions other than cobalt ions which may also be radio-active.

It is disclosed, for example in the mentioned German Offenlegungsschrift, that by the use of acids, alkalis or by the action of light the red metal-free corrinoids can be converted irreversibly into yellow metal-free corrinoids which are characterised by main absorptions $\lambda_{max}$ of 480 and 290 nm. Moreover, patent application Ser. No. 127,365 (Process for obtaining metal-free corrinoids) of the same owner and the same date of filing, discloses that these yellow metal-free corrinoids can also be obtained from the culture medium of Rhodopseudomonas strains. These yellow metal-free corrinoids cannot then be changed back or converted into red metal-free corrinoids, as can be learned, for example, from the mentioned German Offenlegungsschrift. It was also previously impossible to convert them into the metal corrinoids corresponding to the red metal-free corrinoids.

According to the invention a process is now available according to which yellow metal-free corrinoids can be converted into red metal corrinoids. The process is characterised in that in a liquid medium yellow metal-free corrinoids having main absorptions $\lambda_{max}$ of 480 and 290 nm are (a) reacted with complex-forming metal ions to give yellow metal corrinoids, and (b) the yellow metal corrinoids formed are treated with alkali, affording red metal corrinoids.

Water and alcohols, such as ethanol, and mixtures thereof may serve as the liquid reaction medium. The expert is conversant with the reaction of metal-free corrinoids and complex-forming metal ions; see, for example, German Offenlegungsschriften Nos. 1 642 749 and 2 520 722; Koppenhagen et al., J. Biol. Chem., 245 (1970) 5865–5867, 246 (1971) 3075–3077, 248 (1973) 7999–8002 and 249 (1974) 6532–6540; and Dresow, Dissertation, Braunschweig 1978. The progress of the alkaline treatment can be regulated or monitored by the expert by measuring the characteristic absorption maxima in the visible range ($\alpha$ and $\beta$ bands). The alkaline treatment can be carried out, for example, in aqueous medium at a pH of 9 to 13, preferably 10 to 11.

In the process according to the invention the starting materials used may be yellow metal-free corrinoids which (a) have been formed in microbiological processes, or (b) have been produced by converting with the aid of alkali red metal-free corrinoids formed in microbiological processes and having main absorptions $\lambda_{max}$ of 524, 498 and 329 nm or (c) have been produced synthetically or semi-synthetically.

Cobalt ions or rhodium ions, which may optionally be radio-active, may be used as complex-forming metal ions; to form red metal corrinoids using different metal ions, see, for example, the following publications: German Offenlegungsschrift Nos. 1 642 749; German Offenlegungsschrift 2 520 722; Koppenhagen & Pfiffner, J. Biol. Chem., 246 (1971) 3075–3077; Koppenhagen et al., J. Biol. Chem., 248 (1973) 7999–8002; Koppenhagen et al., J. Biol. Chem., 249 (1974) 6532–6540.

In one embodiment of the process according to the invention, the alkaline treatment of the yellow metal-containing corrinoids can be performed with a cyanide that is soluble in liquid medium, for example an alkali metal cyanide or ammonium cyanide. Because cyanides give an alkaline reaction, their action leads to the conversion of the yellow metal corrinoids into the red metal corrinoids and at the same time an addition of cyanide to the complexed metal ion.

In the process according to the invention, the yellow metal-free corrinoid which can be obtained from the metal-free analogue of cobalamine when it is treated, for example, with an alkali can be used for starting material. In that case, the process according to the invention therefore results in cobalamine and analogous metal corrinoids which differ from cobalamine as regards the complexed metal ion. According to Römpp, Chemie-Lexikon, 7th edition, Stuttgart 1972, page 690 (and other literature), corrinoids and "red corrinoids" have the structural feature that four partially hydrogenated pyrrole rings are so linked to one another that a hexa-unsaturated 15-membered ring is formed.

It is assumed that with the yellow metal-free and metal-containing corrinoids the chromophore of the red metal-free and metal-containing corrinoids is interrupted by the formation of a c-lactam at the B-ring incorporating the 5 and 6 positions. The alkaline treatment according to the invention presumably leads to the splitting off of protons in the 5-position and to the splitting of the lactam ring at ring B, as seen from the following reaction scheme:

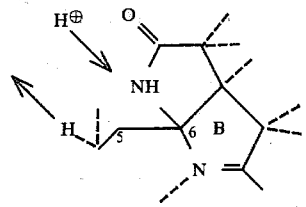

For the nomenclature refer to IUPAC, J. Biol. Chem., 241 (1966) 2999 and Biochem., 13 (1974) 1555.

The invention is explained in detail below by way of an example.

EXAMPLE 55 ml of degasified ethanol were rinsed for 15 minutes with argon at room temperature and to it were added 4.79 mg of yellow vitamin $B_{12}$ (which corresponded to the metal-free analogue of cobalamine with the exception that the B-ring carried a lactam ring in accordance with the preceding drawing). Thereafter, 2.8 mg of $CoCl_2.6H_2O$ in 2.5 ml of correspondingly treated ethanol and 12 ml of 0.25% aqueous ammonia were added. The mixture was then heated in a boiling water bath until the strong yellow initial fluorescence had changed to a weakly-coloured yellow-green fluorescence. After cooling, 80 ml of 0.2 M aqueous KCN were added. The alcohol was removed. Desalinisation was carried out with Amberlite, whereupon the resin served to adsorb the vitamin $B_{12}$. After the desorption, the crude product was purified by paper-chromatography; vitamin $B_{12}$ was obtained as the main product.

In the process according to the invention, as starting materials there may be used metal-free yellow corrinoids which are obtained in a process for obtaining metal-free corrinoids optionally in addition to metal-free red corrinoids in which a Rhodopseudomonas variety is cultivated under illumination and the microorganism is separated from the culture medium, the process being characterised by the fact that the metal-free corrinoids formed are isolated from the culture medium in a manner known per se.

The expert is able to isolate, identify and cultivate Rhodopseudomonas strains at any time from natural sources; in this connection reference may be made to the following works:

Weaver et al., Arch. Mikrobiol., 105 (1975) 215;
Biebl & Drews, ZBl. Bakteriol. Parasitenk. Infektionskr. Hygiene, Abt, 2 123 (1969) 452;
Pfennig & Trüper in "Bergey's Manual of Determinative Bacteriology", 8th edition, Baltimore, (1974) 25–65;
Dresow, Dissertation, Braunschweig 1978; and
German Offenlegungsschrift 1 642 749.

The expert is also conversant with the isolation of metal-free corrinoids from liquid media; compare, for example:

Koppenhagen & Pfiffner, J. Biol. Chem., 245 (1970) 5865–5867;
Koppenhagen & Pfiffner, J. Biol. Chem., 246 (1971) 3075–3077;
Koppenhagen et al., J. Biol. Chem., 248 (1973) 7999–8002;
Dresow, Dissertation, Braunschweig 1978; and
German Offenlegungsschrift No. 1 642 749.

Examples of Rhodopseudomonas strains are *Rhodopseudomonas sphaeroides, capsulata* and *pallustris*. The following details can be given for the deposition of the strains specifically named hereinafter:

| Strain | Place of deposit | Deposit number |
|---|---|---|
| Rhodopseudomonas sphaeroides | DSM Gottingen | 158 |
| Rhodopseudomonas capsulata | DSM Gottingen | 155 |

In obtaining metal-free corrinoids it is important to work with as small as possible a concentration of Fe in the production medium and with Co substantially excluded. Thus, one embodiment of the process provides for a specific depletion of Fe and Co; in this case, starting from a culture of the parent strain (starting culture), in succession several (for example 4 to 9) precultures (sequential cultures) and finally the production culture (last sequential culture) are prepared, in each case by inoculating a nutrient medium, to which in particular no compound of metals of the VIIIth group of the Periodic Table has been added, with a part (for example 5 to 25%, and especially 10%) of the preceding culture. In a specific embodiment of the process, the sequential culture in which an extra-cellular minimum concentration of metal-free corrinoids of 0.1 mg/liter, preferably 0.5 mg/liter and especially 1 mg/liter, is obtainable is selected as the final production culture or as the inoculation culture for the production culture.

On the other hand, the starting culture which has been used to initiate this gradual depletion of Fe and Co ions can be kept as the parent culture in a nutrient medium to which ions or compounds of metals belonging to the VIIIth group of the Periodic Table (for example iron ions) have also been added such as the medium described by Pfennig in Arch. Mikrobiol., 100 (1974) 197–206, or appropriately supplemented or modified media.

According to German Offenlegungsschrift No. 1 642 749, when isolating the metal-free corrinoids a light intensity of 107.6 lux should not be exceeded. Since the process is directed to extra-cellular metal-free corrinoids that are exposed to light, in that process the light intensity used for the illumination is less than the light intensity of, for example 2000 to 4000, especially 3000, lux conventionally used in the cultivation of phototrophic micro-organisms for obtaining intra-cellular metal-free corrinoids, compare, for example, with the known state of the art:

Koppenhagen & Pfiffner, J. Biol. Chem., 245 (1970) 5865–5867;
Koppenhagen & Pfiffner, J. Biol. Chem., 246 (1971) 3075–3077;
Koppenhagen, Dechema Grundkursus Biotechnologie, (1977) 75–92;
Toohey, Proc. Nat. Sci., 54 (1965) 934–942; and
Toohey, Fed. Proc. (1966) 1628–1632.

Surprisingly, in the process it is possible, however, first of all to illuminate the culture with the light intensity of for example 2000 to 4000, especially 3000, lux, customary in the cultivation of phototrophic micro-organisms for obtaining intra-cellular metal-free corrinoids, and thereafter to illuminate the culture with a light intensity that is not so great in comparison. This embodiment of the process makes use of the fact that at the start of the growth phase hardly any metal-free corrinoids are secreted into the culture medium. A light intensity reduced by 50 to 90%, and especially by 60 to 80%, can be used, for example a light intensity of 1500 lux or less, 1000 lux or less or 500 lux or less.

If it is desired to reduce the light intensity only during the cultivation, the light intensity may advantageously be reduced when the optical density at 660 nm has reached a value in the range of from 2 to 4, especially in the range of from 2.5 to 3.

According to German Offenlegungsschrift No. 1 642 749, a pH of more than 7 should be avoided when isolating metal-free corrinoids. Although the process is directed to the production of extra-cellular metal-free corrinoids, it has unexpectedly been discovered that operation can be carried out very well with the precultures and production cultures in a neutral or weakly alkaline range. According to one embodiment of the process, the pH is not re-adjusted when it changes and according to a different embodiment of the process the pH can be regulated to be in the range of from 7.5 to 9.0 and especially in the range of from 7.5 to 8.5.

By means of the process, the yield of metal-free corrinoids can be increased sixty-fold; thus, for example, for *Rhodopseudomonas sphaeroides* more than 5 mg/liter have already been obtained and for *Rhodopseudomonas capsulata* more than 1.5 mg/liter have been obtained.

The process of Ser. No. 127,365 is explained in greater detail below by way of an Example.

Culture medium and growth conditions

The parent cultures were kept as liquid cultures in a chemically defined mineral medium prepared according to Pfennig (Arch. Mikrobiol., 100 (1974) 197–206, to which yeast extract (from Difco; 0.1% weight/volume)

and disodium succinate (0.1% weight/volume) had been added. Sodium thiosulphate was left out. Sequential cultures were prepared every month from the parent cultures and incubated for 48 hours under light at 27° C.; they were stored at 4° C.

To produce the extra-cellular corrinoids, a modified Lascelles medium was used containing per liter of final volume the following constituents:

5.38 g DL- malic acid;
500 mg potassium dihydrogen phosphate;
500 mg dipotassium hydrogen phosphate;
800 mg diammonium hydrogen phosphate;
200 mg magnesium sulphate.$7H_2O$;
40 mg calcium chloride;
2.86 mg boric acid;
1.81 mg manganese dichloride.$4H_2O$;
0.079 mg copper sulphate.$5H_2O$;
0.176 mg $H_2MoO_4.5H_2O$;
0.023 mg $NH_4VO_3$;
1 mg nicotinic acid;
1 mg thiamine hydrochloride; and
10 μg biotin.

The pH was adjusted to 6.8 with 2 N NaOH.

To deplete the parent cultures of Fe and Co, precultures (or sequential cultures) were prepared 4 to 9 times in the said medium. Cultivation was carried out in 1 liter capacity flasks (Pyrex) having screw-type closures and filled completely in order to exclude air. The flasks were placed in a water bath that was maintained at a temperature of 27° C. The illumination was carried out with three reflector lamps (100 W), which were so positioned that they provided a uniform light intensity of 3000 lux at the inlet window of the water bath. In each flask the inoculate was 10%. The last stage of the depletion series served as the inoculum for 10-liter production cultures which grew under continuous illumination at 22° C. with no adjustment of the pH. When the cultures had reached an optical density of 3.0 at 660 nm, the initial light intensity of 3000 lux was reduced to 1000 and 600 lux respectively. The cultures were allowed to grow for a total of 300 hours. After this time both strains (DSM 155 and 158) had reached the stationary phase (optical density 6.2 to 6.6), at which no further enrichment of extra-cellular corrinoids was observed. The pH had risen to a value in the range from 8.2 to 8.6.

Further production cultures were allowed to grow in a 350 liter tube photoreactor, which had been specially constructed for large-scale cultivation of phototrophic micro-organisms; see Koppenhagen, Dechema Grundkursus Biotechnologie, (1977) 75–92.

Isolation with *Rhodopseudomonas sphaeroides*

After separating the cells by centrifugation, the reddish-brown supernatant liquid (which showed a strong reddish-orange fluorescence under ultra-violet light) was set to pH 3. Metal-free corrinoids together with large quantities of porphyrins and other hydrophobic compounds were adsorbed on Amberlite (XAD-2; 100 to 200 μm). The resin was washed until neutral; the corrinoids and the partially entrained porphyrins were eluted with tert.-butyl alcohol (20%). The butanol was removed under reduced pressure; the aqueous residue was introduced into a column charged with DEAE cellulose in the acetate form. Riboflavins and other yellow products, that were not characterised further, were quickly eluted with water, the porphyrins and the metal-free corrinoids being retained quantitatively at the top of the column. The corrinoids were separated from the mass of porphyrins by eluting with 0.5 N acetic acid. The acidic eluate was transferred to a small XAD-2 bed (50 to 100 μm) from which the corrinoids were eluted with tert.-butyl alcohol (10%). The concentrated eluate was then again chromatographed on DEAE cellulose in the acetate form. The elution with aqueous acetic acid (1%) yielded four fractions of metal-free corrinoids with a total yield of 3.5 mg/liter of culture filtrate.

Details of the fractions obtained are as follows:
fraction 1: red pentacarboxylic acid;
fraction 2: yellow pentacarboxylic acid;
fraction 3: red hexacarboxylic acid; and
fraction 4: yellow hexacarboxylic acid.

The two red carboxylic acids were crystallised from aqueous solution as thin orange needles; main bands $\lambda_{max}$:524, 498 and 329 nm; $\epsilon \times 10^{-3}$: 20.14, 18.64 and 48.37. The absorption spectra of the yellow fractions corresponded very significantly to those that were found for the yellow conversion products of the red decobalto corrinoids after treating with alkali (Toohey in Proc. Nat. Sci., 54 (1965) 934–942 and Fed. Proc., 25 (1966) 1628–1632); main absorption $\lambda_{max}$:480, 462 (shoulder) and 290 nm; $\epsilon \times 10^{-3}$:24.68, 23.58 and 39.72.

Isolation with *Rhodopseudomonas capsulata*

The method of isolating extracellular metal-free corrinoids was the same as that with *Rhodopseudomonas sphaeroides*. In addition to the hexa- and pentacarboxylic acids, this micro-organism yielded also tetra-, tri-, di- and monocarboxylic acids and several neutral and basic products. After adsorption on an XAD-2 column and elution, the acid corrinoids were retained on DEAE cellulose in the acetate form and fractionated by elution with aqueous acetic acid (1%). The aqueous eluate contained the neutral and basic corrinoids which were separated off. The total yield of extracellular corrinoids was 0.4 mg/liter of culture filtrate.

We claim:

1. Process for producing red metal corrinoids, consisting essentially of the steps of
    (a) reacting yellow metal-free c-lactam-at-the-B-ring-corrinoids having main absorptions $\lambda_{max}$ of 480 and 290 nm in a liquid medium with complex-forming metal ions to give yellow metal-containing corrinoids, and
    (b) treating the metal corrinoids formed with alkali.

2. Process according to claim 1, wherein said yellow metal-free c-lactam-at-the-B-ring-corrinoids used as starting materials are selected from the group consisting of
    (a) those corrinoids which have been formed in microbiological processes and
    (b) those corrinoids which have been produced by converting, with the aid of alkali, red metal-free corrinoids formed in microbiological processes and having main absorptions $\lambda_{max}$ of 524, 498 and 329 nm.

3. Process according to claim 1 or 2, wherein said complex-forming ions are cobalt or rhodium ions which are optionally radio active.

4. Process according to claim 1 or 2, wherein said alkali treatment of said yellow metal-containing corrinoids is performed with an alkali-reacting cyanide that is soluble in said liquid medium.

5. Process according to claim 2, wherein said yellow metal-free corrinoids used as starting materials are obtained from the metal-free analogue of cobalamine by treatment with an alkali in accordance with claim 2 (b).

6. Process according to claim 3, wherein said alkali treatment of said yellow metal-containing corrinoids is performed with an alkali-reacting cyanide that is soluble in said liquid medium.

7. Process according to claim 4, wherein said alkali-reacting cyanide is selected from the group consisting of alkali metal cyanide and ammonium cyanide.

8. Process according to claim 6, wherein said alkali-reacting cyanide is selected from the group consisting of alkali metal cyanide and ammonium cyanide.

9. Process according to claim 1 or 2 wherein said treating the metal corrinoids formed with alkali is conducted in an aqueous medium at a pH of 9 to 13.

10. Process according to claim 9 wherein said pH is from 10 to 11.

11. Process for producing red metal corrinoids consisting essentially of
(a) reacting yellow metal-free c-lactam-at-the-B-ring-corrinoids having main absorptions) $\lambda_{max}$ of 480 and 290 nm, selected from the group consisting of
   (1) those corrinoids formed in microbiological processes, and
   (2) those corrinoids produced by alkaline conversion of red metal-free corrinoids formed in microbiological processes and having main absorptions $\lambda_{max}$ of 524, 498 and 329 nm, in a liquid medium with complex-forming cobalt or rhodium ions to give yellow metal-containing corrinoids,
(b) treating said yellow metal-containing corrinoids with alkali in an aqueous medium at a pH of 9 to 13, and
(c) recovering red metal corrinoids.

12. Process for producing red metal corrinoids consisting essentially of
(a) reacting yellow metal-free c-lactam-at-the-B-ring-corrinoids having main absorptions $\lambda_{max}$ of 480 and 290 nm, produced from vitamin $B_{12}$, in a liquid medium with cobalt ions to give yellow cobalt-containing corrinoids,
(b) treating said yellow cobalt-containing corrinoids with an alkali metal cyanide in an aqueous medium at a pH of 9 to 13, and
(c) recovering a red metal corrinoid vitamin $B_{12}$.

* * * * *